United States Patent
Zhou

(10) Patent No.: US 10,610,109 B2
(45) Date of Patent: Apr. 7, 2020

(54) EMOTION REPRESENTATIVE IMAGE TO DERIVE HEALTH RATING

(71) Applicant: Futurewei Technologies, Inc., Plano, TX (US)

(72) Inventor: Yan Zhou, Santa Clara, CA (US)

(73) Assignee: Futurewei Technologies, Inc., Plano, TX (US)

( * ) Notice: Subject to any disclaimer, the term of this patent is extended or adjusted under 35 U.S.C. 154(b) by 0 days.

(21) Appl. No.: 15/870,634

(22) Filed: Jan. 12, 2018

(65) Prior Publication Data

US 2019/0216334 A1 Jul. 18, 2019

(51) Int. Cl.
*A61B 5/01* (2006.01)
*A61B 5/00* (2006.01)
*A61B 5/16* (2006.01)
*G16H 50/20* (2018.01)
*G06F 16/583* (2019.01)
(Continued)

(52) U.S. Cl.
CPC .............. *A61B 5/01* (2013.01); *A61B 5/0022* (2013.01); *A61B 5/0064* (2013.01); *A61B 5/165* (2013.01); *A61B 5/7267* (2013.01); *A61B 5/7278* (2013.01); *A61B 5/742* (2013.01); *G06F 16/583* (2019.01); *G16H 50/20* (2018.01); *G06K 9/00221* (2013.01);
(Continued)

(58) Field of Classification Search
CPC ... A61B 5/0006; A61B 5/0022; A61B 5/0024; A61B 5/1176; A61B 5/165; G06F 19/3418; G06K 9/00335; G06K 9/6292; G06T 2207/20081; G06T 2207/20084
See application file for complete search history.

(56) References Cited

U.S. PATENT DOCUMENTS

2015/0199010 A1* 7/2015 Coleman .............. A61B 5/0006 345/156
2016/0350801 A1* 12/2016 Vincent .............. G06Q 30/0251
(Continued)

FOREIGN PATENT DOCUMENTS

CN 107220591 A 9/2017
CN 107392151 A 11/2017
(Continued)

OTHER PUBLICATIONS

"International Application No. PCT/CN2019/071666, International Search Report and Written Opinion dated Apr. 16, 2019", (Apr. 16, 2019), 10 pgs.

*Primary Examiner* — Ross Varndell
(74) *Attorney, Agent, or Firm* — Schwegman Lundberg & Woessner, P.A.

(57) ABSTRACT

A computer implemented method of generating a personalized health rating for a person uses one or more processors. The one or more processors execute instructions to perform the method including obtaining, by the one or more processors, measured data associated with the person, obtaining, by the one or more processors, a facial image of the person, extracting, by the one or more processors, emotional based features from the facial image, using a deep learning model trained on emotion labeled facial images to associate an emotional state with the extracted features to generate emotional data, and fusing, by the one or more processors, the measured data with the emotional data to generate the personalized health rating.

19 Claims, 8 Drawing Sheets

(51) Int. Cl.
*G16H 50/30* (2018.01)
*G06K 9/00* (2006.01)
(52) U.S. Cl.
CPC ............... *G06T 2207/10004* (2013.01); *G06T 2207/10024* (2013.01); *G16H 50/30* (2018.01)

(56) References Cited

U.S. PATENT DOCUMENTS

2017/0238860 A1* 8/2017 el Kaliouby ......... A61B 5/0077
2017/0270664 A1* 9/2017 Hoogi ....................... G06T 7/10

FOREIGN PATENT DOCUMENTS

CN          107463874 A    12/2017
WO    WO-2004030532 A1     4/2004

* cited by examiner

PAIN

DEPRESSION

EMOTION REPRESENTATIVE IMAGE TO DERIVE HEALTH RATING

TECHNICAL FIELD

The present disclosure is related deriving a personalized health rating and in particular to including an emotional state of a person by use of emotion representative facial images of the person to derive the health rating.

BACKGROUND

Personalized health ratings are very important in smart family care applications. The advantages of personalized in-home family care include convenience for users to monitor and evaluate their health on a daily basis without going to the hospital. Most vital signs on which personalized health ratings are based can be taken at home, allowing for a more pleasant experience as opposed to taking vital signs in a more formal medical care facility, such as a hospital, which may be quite a distance from the user's home.

SUMMARY

Various examples are now described to introduce a selection of concepts in a simplified form that are further described below in the detailed description. The Summary is not intended to identify key or essential features of the claimed subject matter, nor is it intended to be used to limit the scope of the claimed subject matter.

According to one aspect of the present disclosure, a computer implemented method of generating a personalized health rating for a person uses one or more processors. The one or more processors execute instructions to perform the method including obtaining, by the one or more processors, measured data associated with the person, obtaining, by the one or more processors, a facial image of the person, extracting, by the one or more processors, emotional based features from the facial image, using a deep learning model trained on emotion labeled facial images to associate an emotional state with the extracted features to generate emotional data, and fusing, by the one or more processors, the measured data with the emotional data to generate the personalized health rating.

Optionally, in any of the preceding aspects, a further implementation of the aspect includes normalizing the facial image prior to extracting the emotional based features such that the image is compatible with the measured data.

Optionally, in any of the preceding aspects, a further implementation of the aspect includes removing noise from the image, wherein such noise comprises background pixels.

Optionally, in any of the preceding aspects, a further implementation of the aspect includes wherein the deep learning model comprises a 3-layer convolutional neural network.

Optionally, in any of the preceding aspects, a further implementation of the aspect includes wherein the facial image comprises multiple images captured by a networked camera.

Optionally, in any of the preceding aspects, a further implementation of the aspect includes wherein the multiple images are captured continuously while the networked camera is enabled, and the personal health rating is calculated as a function of the multiple images.

Optionally, in any of the preceding aspects, a further implementation of the aspect includes wherein the networked camera is incorporated in a wireless mobile device, and wherein the facial images are received from the mobile device.

Optionally, in any of the preceding aspects, a further implementation of the aspect includes wherein the measured data comprises environmental data associated with the person, vital signs of the person, and daily activity of the person.

Optionally, in any of the preceding aspects, a further implementation of the aspect includes wherein fusing the measured data and emotional data comprises using statistically sound information fusion with prioritized weighting of the data, and wherein the personalized health rating comprises a mental health rating.

According to one aspect of the present disclosure, a device includes a memory storage comprising instructions and one or more processors in communication with the memory. The one or more processors execute the instructions to obtain measured data associated with a person, obtain a facial image of the person, extract emotional based features from the facial image, use a deep learning model trained on emotion labeled facial images to associate an emotional state with the extracted features to generate emotional data, and fuse the measured data with the emotional data to generate a personalized health rating.

Optionally, in any of the preceding aspects, a further implementation of the aspect includes normalizing the facial image prior to extracting the emotional based features such that the image is compatible with the measured data.

Optionally, in any of the preceding aspects, a further implementation of the aspect includes wherein the deep learning model comprises a 3-layer convolutional neural network.

Optionally, in any of the preceding aspects, a further implementation of the aspect includes a camera communicatively coupled to the processor to obtain the facial image, and wherein the facial image comprises multiple images.

Optionally, in any of the preceding aspects, a further implementation of the aspect includes wherein fusing the measured data and emotional data comprises using statistically sound information fusion with prioritized weighting of the data and wherein the personalized health rating comprises a mental health rating.

Optionally, in any of the preceding aspects, a further implementation of the aspect includes wherein the device is a wireless mobile device with an integrated camera.

According to one aspect of the present disclosure, a non-transitory computer-readable media stores computer instructions for generating a personalized health rating. When the instructions are executed by one or more processors, the one or more processors perform the steps of obtaining measured data associated with a person, obtaining a facial image of the person, extracting emotional based features from the facial image, using a deep learning model trained on emotion labeled facial images to associate an emotional state with the extracted features to generate emotional data, and fusing the measured data with the emotional data to generate the personalized health rating.

Optionally, in any of the preceding aspects, a further implementation of the aspect includes normalizing the facial image prior to extracting the emotional based features such that the image is compatible with the measured data.

Optionally, in any of the preceding aspects, a further implementation of the aspect includes removing noise from the image, wherein such noise comprises background pixels.

Optionally, in any of the preceding aspects, a further implementation of the aspect includes wherein the deep learning model comprises a 3-layer convolutional neural network.

Optionally, in any of the preceding aspects, a further implementation of the aspect includes wherein the facial image comprises multiple images captured by a networked camera and wherein fusing the measured data and emotional data comprises using statistically sound information fusion with prioritized weighting of the data and wherein the personalized health rating comprises a mental health rating.

DETAILED DESCRIPTION

In the following description, reference is made to the accompanying drawings that form a part hereof, and in which is shown by way of illustration specific embodiments which may be practiced. These embodiments are described in sufficient detail to enable those skilled in the art to practice the invention, and it is to be understood that other embodiments may be utilized and that structural, logical and electrical changes may be made without departing from the scope of the present invention. The following description of example embodiments is, therefore, not to be taken in a limited sense, and the scope of the present invention is defined by the appended claims.

The functions or algorithms described herein may be implemented in software in one embodiment. The software may consist of computer executable instructions stored on computer readable media or computer readable storage device such as one or more non-transitory memories or other type of hardware based storage devices, either local or networked. Further, such functions correspond to modules, which may be software, hardware, firmware or any combination thereof. Multiple functions may be performed in one or more modules as desired, and the embodiments described are merely examples. The software may be executed on a digital signal processor, ASIC, microprocessor, or other type of processor operating on a computer system, such as a personal computer, server or other computer system, turning such computer system into a specifically programmed machine.

Previously, personalized health ratings have mainly calculated based on environmental information, vital sign information, and daily activity monitoring information. Such information was focused on physiological aspects of human fitness. However, mental fitness was not properly incorporated into the personalized health rating, even though mental fitness is a very important part of the overall health. A main difficulty in attempting to incorporate mental health into personalized health ratings is the difficulty of observing mental health using machines such as robots or computers.

Embodiments of the inventive subject matter combine measurable data related to a person's physiological state with facial images representing the person's emotional state using emotion recognition in the computer vision field, to calculate a personal health rating. The measurable data may include information of all kinds associated with the person, such as environment, vital signs, and daily activities for example. The measurable data and emotional state data is then fused by statistically sound information fusion methods.

Figure 1:
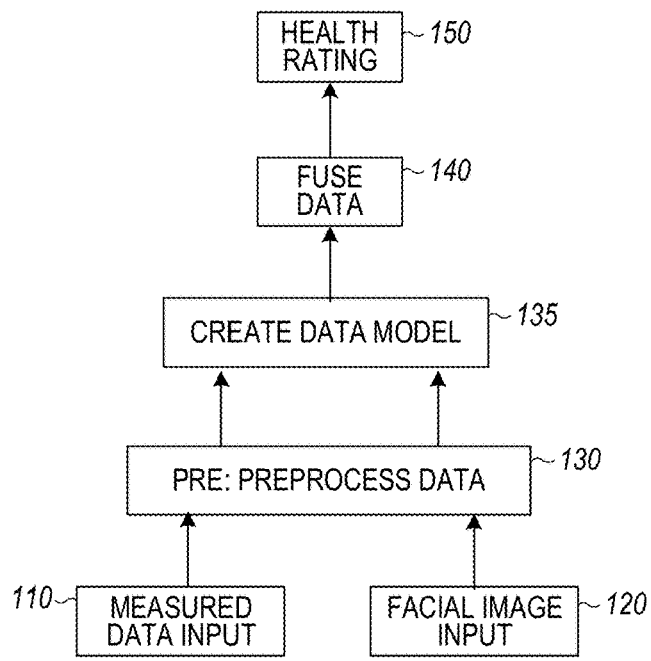
FIG. 1 is a block flow diagram of a system for generating a personalized health rating that includes an emotional health component according to an example embodiment.

FIG. 1 is a block flow diagram of a system 100 for generating a personalized health rating that includes an emotional health component. System 100 includes a measured data input 110 and a facial image input 120. The measured data input 110 may include environment data, vital signs, and activity information associated with the person. Sensors may provide the data in one embodiment, such as by wearable devices including fitness bands, internet of things enabled measurement devices, or other devices that may measure data associated with the person and provide that data to measured data input 110.

The measured data and facial image input are preprocessed by a pre-processing module 130 to calibrate, remove noise, extract image features, and normalize the measured data and facial image input. A data model is created by a data module 135 that processes the image features and extracts non-image features from the measured data. The processed image features and non-image features in data module 135 are also fused at 140 to provide a health rating 150.

Figure 2:
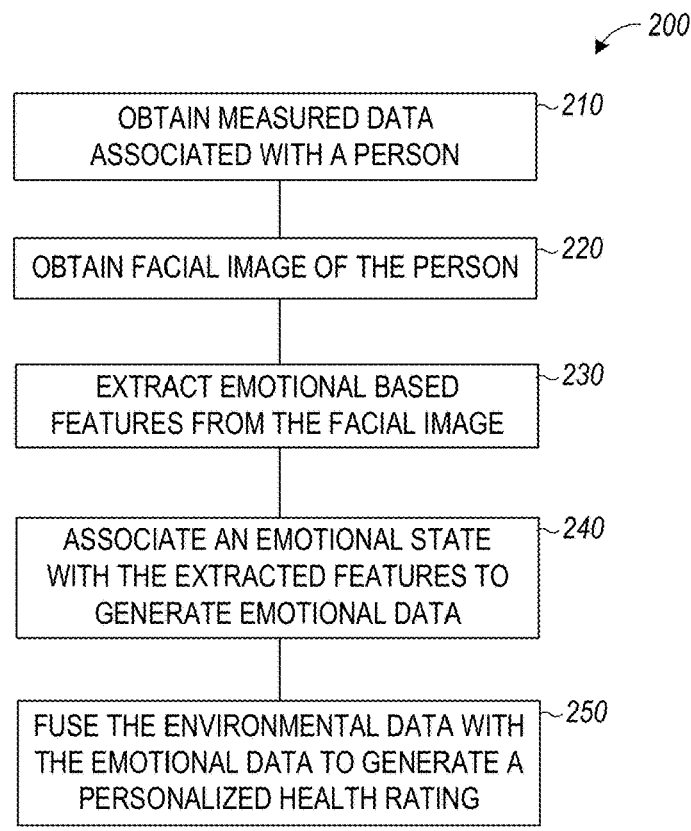
FIG. 2 is a flowchart illustrating a method of generating a personalized health rating for a person according to an example embodiment.

FIG. 2 is a flowchart illustrating a method 200 of generating a personalized health rating for a person at a simplified level. Method 200 may be performed by one or more specifically programmed machines, referred to as processing resources. The processing resources may be incorporated in a mobile device, such as a robot, cellular phone, touchpad, or other device. Processing resources may further be divided between the mobile device and network resources, such as cloud resources.

Method 200 includes operations 210 that obtain measured data associated with the person. The measured data may be obtained from measurements of vital signs of the person, such as heart rate, body mass index, glucose, height, weight, temperature, blood pressure, etc. Further measured data may include environmental data, such as air quality and water quality associated with the person. Daily activity, such as sleep, diet, and exercise are examples of further measured data.

In some embodiments, the measured data may be provided by networked wireless devices, also represented by measured data input 110, or may be hand entered or spoken into a speech recognition program also represented by measured data input 110. Such devices may include thermometers, EKG machines, blood pressure cuffs, wearable devices, weight scales, glucose meters, and the like.

Operations 220 obtain a facial image of the person. The facial image may be obtained via a camera, also represented by facial image input 120. The camera may be mounted on a mobile device, such as a cellular phone, computer, touchpad, robot, or other device suitable for obtaining an image of the face of the person. In some embodiments, the facial images may be provided periodically, such as once per day, or several times a day, such as each time a person uses the device containing the camera. In still further embodiments, the facial images may be obtained continuously while the camera is enabled, such as being in an on state and connected to a network if the health rating is calculated by networked based computing or processing resources or queued for later processing. In some embodiments, the camera may be incorporated into the device with calculation of the health rating being done with computing resource of the device.

Operations 230 extract emotional based features from the facial image or images. Operations 240 use processing resources programmed to use a deep learning model trained on labeled emotion based features of a set of training facial images to associate an emotional state with the extracted features to generate emotional data. The emotional based features may be extracted by a trained deep learning model trained with multiple labeled images of faces. The images may be labeled with various emotional states, such as happy, sad, depressed, scared, angry, fearful, surprised, etc. In one embodiment, the deep learning model may be a three layer CNN (convolutional neural network), or other type of deep learning networks, such as ResNet, Inception, Exception, VGG 16, and others. The deep learning model may also be used to associate the emotional state with the extracted features to generate emotional data. In machine learning, a convolutional neural network (CNN, or ConvNet) is a class of deep, feed-forward artificial neural network that have successfully been applied to analyzing visual imagery.

In operations 250, the environmental data are fused with the emotional data. The fused data may be used as a personalized health rating or further processed to generate the personalized health rating. The personalized health rating may be used for many different applications, such as elderly care, infant care, health management by the person or a care provider caring for the person.

In some embodiments, facial images may be captured periodically as described above. The health rating may be calculated with each such image received. In further embodiments, facial images may be obtained continuously while the camera is operating, and the image input is enabled. The health rating may then also be continuously calculated or updated, such as with each new image, or periodically, or after receipt of a specified number of images. One example might be every 30 minutes, or receipt of 30,000 images, which roughly corresponds to 30 minutes of 30 frame per second video.

Figure 3:
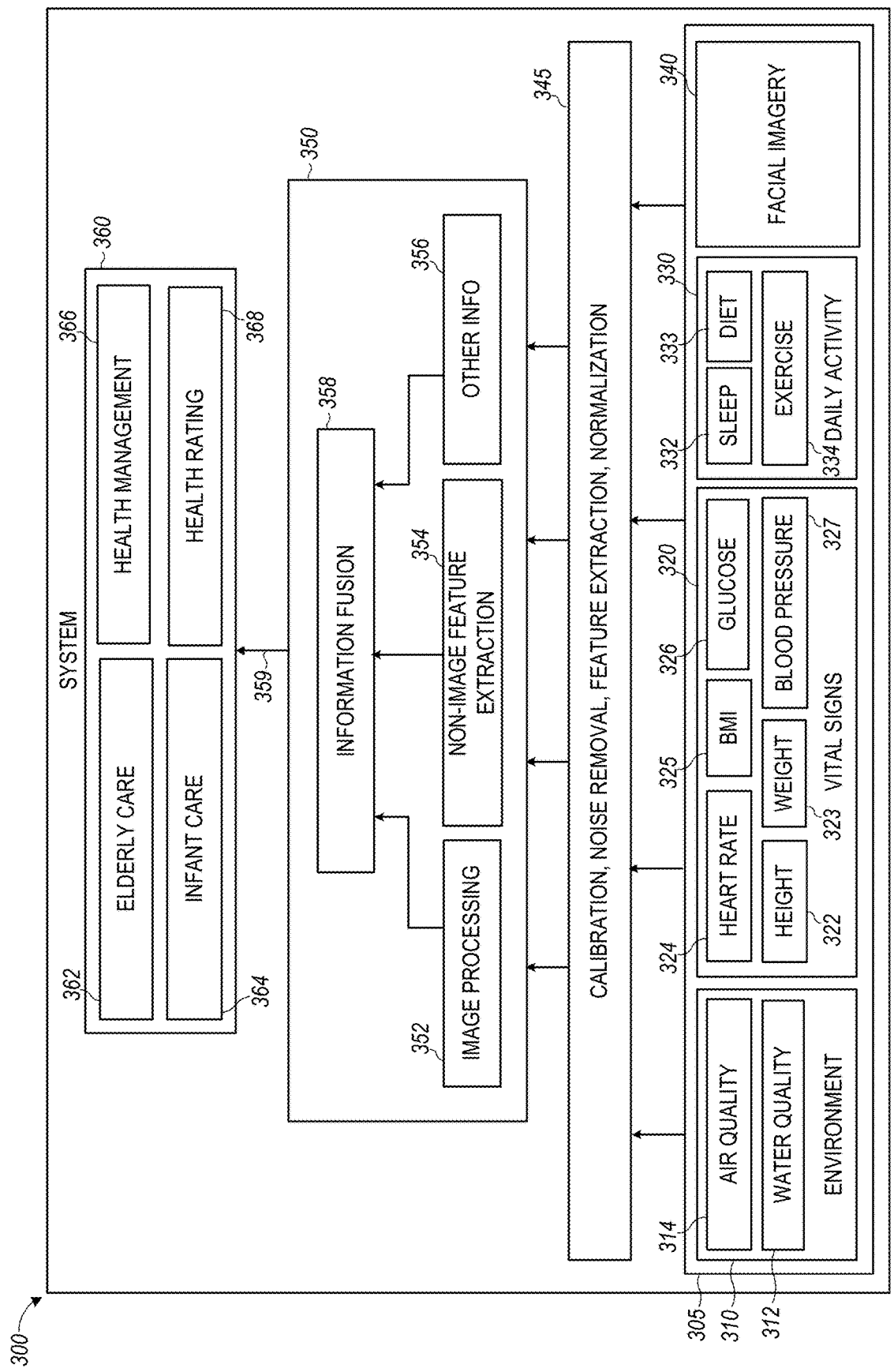
FIG. 3 is a detailed block diagram illustrating a system for generating a personalized health rating that includes an emotional health component according to an example embodiment.

FIG. 3 is a detailed block diagram illustrating a system 300 for generating a personalized health rating that includes an emotional health component. System 300 includes an information input layer 305 to receive or obtain measured information that will be processed to obtain a personalized health rating that includes physiological and emotional states. Input layer 305 in one embodiment may include an environmental input 310 to provide a water quality measurement input 312 and an air quality measurement input 314. Environmental input 310, such as air quality input 314, may include pollen measurement, UV index measurements, air temperature, humidity, and other environmental measurements not known or further discovered that are associated with a person and may affect their health when exposed to such an environment. Measurement for water quality may include lead content of water, or other chemicals which may affect health of the person exposed to such water.

Input layer 305 may also include vital sign inputs 320, which may include one or more of height 322, weight 323, heart rate 324, body mass index (BMI) 325, glucose level 326, and blood pressure 327 for example. Other vital signs may be included in further embodiments. Some of these inputs of vital sign inputs 320 may comprise inputs from associated sensors such as a heart rate monitor that provides heart rate input 324 or inputs that are entered manually or otherwise obtained (e.g., height 322, weight 323 and BMI 325). BMI 325, for example, may be entered or it may be provided by a calculation module that determines the BMI from other inputs such as height 322 and weight 323).

Input layer 310 may further include measured information related to daily activity 330 of the person. The measured information may include information related to sleep 332, diet 333, and exercise 334. The environmental measured information, vital sign information, and daily activity measured information may be provided by one or more sensors, such as wearable devices, Internet Of Things devices, and other non-networked devices. The measured information may also be provided subjectively (describing pain levels for example) or objectively by the person using the non-networked devices or simply from counting heartbeats from feeling a pulse, or from third party observers of the person in various embodiments.

Input layer 310 in one embodiment further includes a facial image input 340. Facial images may be obtained via a camera, also represented by facial image input 340. The camera may be mounted on a mobile device, such as a cellular phone, computer, touchpad, robot, or other device suitable for obtaining an image of the face of the person. In some embodiments, the facial images may be provided periodically. In further embodiments, the facial images may be obtained several times a day, such as each time a person uses the device containing the camera.

Measured and stored data from the input layer 310 may be provided to a preprocessing layer 345. Preprocessing layer 345 provides calibration for the measured input, such as environmental, vital signs, and daily activity measured data. Calibration may be used to calibrate sensors such that measurements from such sensors are accurate. Noise removal may be used to remove background pixels from facial images. The pre-processing layer 345 may also provide for normalization of the image features and measured data to be compatible for further processing. The normalization in one embodiment may balance pixel intensity to have values between 0 and 1, along with other measured data, such that all data is normalized and hence compatible for further processing. Training images for training the deep learning network may also be normalized in the same manner.

System 300 may also include a data model 350. The data model 350 provides image processing 352 that down samples facial images, as all the information in an image is not required for determining emotional state from multiple images. Image processing 352 uses the deep learning network to determine how much time the person is in each emotion state during a period of time, or as a percentage of time from multiple time stamped image features. Image processing 352 performs image feature extraction on the images to extract known features for later use by a deep learning network to gauge emotional state information from the images based on the features. The features may be identified during training of the deep learning network.

A non-image feature extraction module 354 extracts features from the measured data. If the measured data includes electrical measurements, such as an EKG signal, an FFT or wavelet transformation may be performed to derive or extract features. Other information 356 may be provided, such as information about the person, including known conditions or previous assessments of the health of the person.

Some of the features may be obtained simply by comparing measured data to thresholds, such as temperature thresholds which are assigned numeric values. Other features may be represented by the raw measurement itself, or ranges of measurements may be assigned different values for fusing to determine the personal health rating. In still further embodiments machine learning networks may be utilized for extracting features from complex data that is not easily mathematically quantified.

The data model 350 also includes an information fusion module 358 that uses the information from image processing 352, measured data feature extraction 354, and other information 356 to generate a health rating 359 that may be used by one or more applications 360 related to elderly care application 362, infant care applications 364, health management applications 366, and health rating applications 368 to name a few. Such applications may make health care recommendations based at least in part on the health rating 359 to the person or to a healthcare professional taking care of the person.

The fusion module 358 may be statistically sound and take into account different weights for the features and information derived from the measured data and facial images.

In one embodiment, the health rating may be calculated or fused by the fusion module 358 in the following manner:

$$S = w\_1 F(x\_1) + w\_2 F(x\_2) + \ldots + w\_n F(x\_n)$$

where S is the health rating or score, such as mental health rating or score, and n is the number of parameters used to calculate the mental health score. The parameters are $x\_1$, $x\_2, \ldots, x\_n$ are the parameters. For example, if the parameters, x, used are sleep duration, body weight, and emotion analysis to calculate the mental health score, n=3. $w\_1, w\_2 \ldots w\_n$ are the weights associated with each parameter. The weights can be set heuristically based on expert experience, or be learned automatically from machine learning algorithms. $F(x\_1), F(x\_2) \ldots F(x\_n)$ are functions to derive a meaningful calculation from each parameter $x\_1$, $x\_2, \ldots x\_n$.

The health rating or score may be a number representative of the mental health of the person, or the overall health of the person taking mental health into account. The rating may be scaled in some embodiments to a score of zero or 1 to 100, with either zero or 1, or 100 being indicative of good or bad health in various embodiments. Other ranges may be used for the scale, such as 0-10 for example.

Figure 4A:
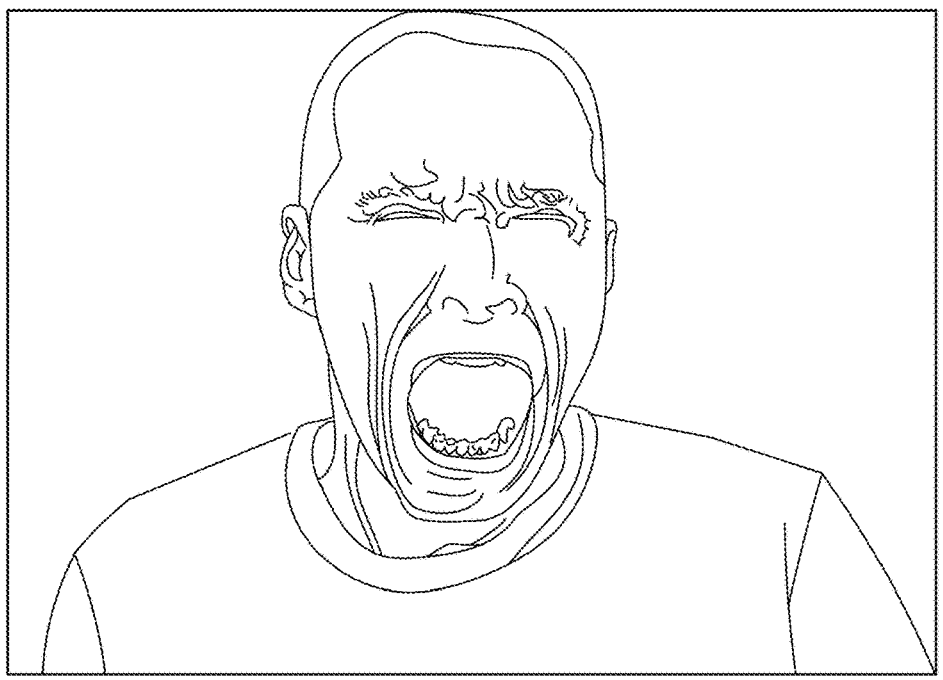
FIGS. 4A and 4B are example labeled facial images representative of pain and depression respectively according to an example embodiment.
Figure 4B:

An example of labeled facial images is shown in FIGS. 4A and 4B. FIG. 4A is an image of a person with a label of the emotion, pain. The image features that may be useful for the deep learning network may include high level features such as furrowed nose between the eyebrows, wide open mouth squinting eyebrows, and other features. Note that in training the deep learning network (DLN), many such images of various persons in pain may be used by the DLN to identify further features associated with the emotion pain.

FIG. 4B corresponds to a person who may be depressed. Some high level features that may be identified are a lack of muscle tension in the face, straight or slightly frowning lips, and other features that may be identified by the DLN during training on multiple depression labeled images. The DLN may be trained using many further emotion labeled images, with various labels as referred to above, such as sad, happy, annoyed, and several others.

Figure 5A:
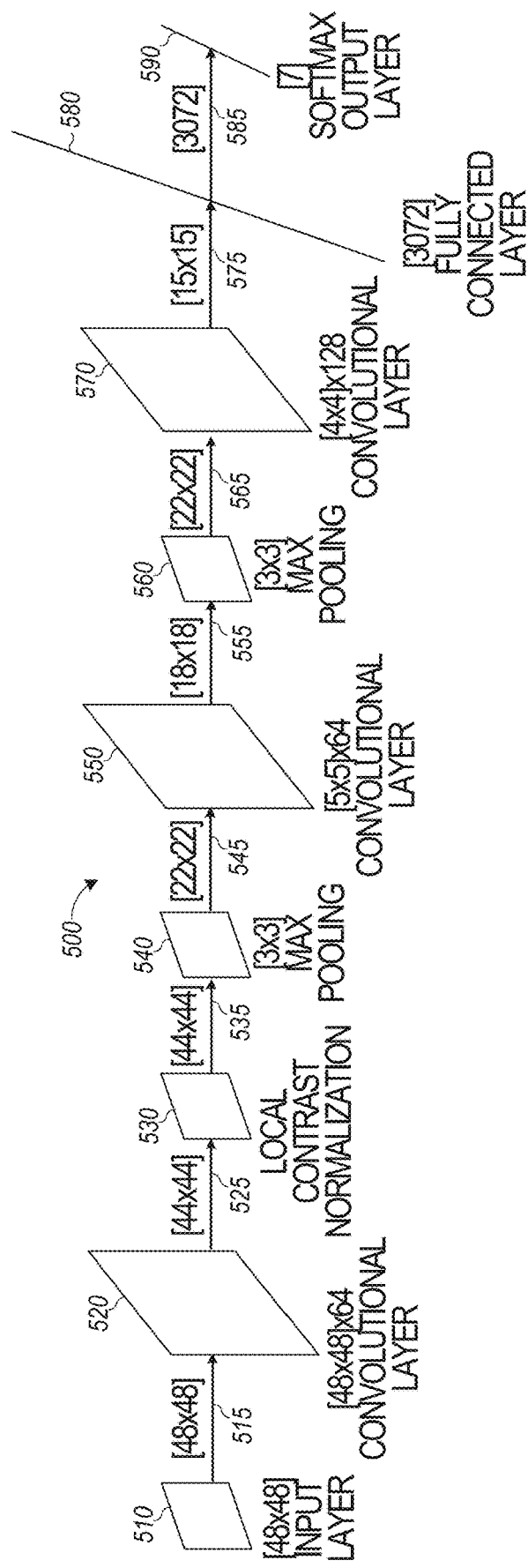
FIG. 5A is block flow diagram of an algorithm pipeline for a deep learning network according to an example embodiment.

FIG. 5A is block flow diagram of an algorithm pipeline for a DLN network 500 for implementation of image processing 352 and optionally non-image feature extraction block 354. DLN network 500 in one embodiment is a 3-layer CNN. The term 3-layer corresponds to the use of three convolutional layers in the network. Convolutional layers identify features at different levels of abstraction, with the first layers looking for such things a straight lines, curved lines, and edges, while later layers identify higher level features that are more likely to be directly associated with identification of the subject, or in this case, emotion associated with the person in the image.

A 48×48 input layer 510 receives image features and provides an output 515 to a [48×48]×64 first convolutional layer 520. The size information (for example: [48×48] on output 515) shows the output size from each step or layer. The information under each layer or step (for example: [48×48]×64 for convolutional layer 520) shows the "task" applied in that step. The [48×48]×64 first convolutional layer 520 provides a [44×44] output 525 to a local contrast normalization layer 530. Note that the numbers in brackets "[ ]" refer to pixels, and a number following the brackets refers to intensity of the pixels in one embodiment. The numbers shown in this example are for example purposes only and may vary in different embodiments. Layer 530 normalizes the [44×44] output and provides such output 535 to a max pooling function 540. The max pooling function 540 partitions the input image into a set of non-overlapping rectangles and, for each such sub-region, outputs at 545 the maximum as a [22×22] max pooling output.

The max pooling output 545 is provided to a second [5×5]×64 convolutional layer 550 that provides an [18×18] output 555. The [18×18] output 555 is provided to a [3×3] max pooling function 560, which provides a [22×22] max pooling output 565. The max pooling output 565 is provided to a [4×4]×128 third convolutional layer 570. Third convolutional layer 570 provides a [15×15] output 575 to a fully connected layer 580 of format [3072].

Fully connected layer 580 looks at the output of the previous layer (which should represent the activation maps of high level features) and determines which features most correlate to a particular class. Basically the fully connected layer determines what high level features most strongly correlate to a particular class and has particular weights such that computing products between the weights and the previous layer, correct probabilities for the different classes are obtained. Note that in this case, the classes correspond to emotions of the person.

Fully connected layer 580 provides a [3072] output 585 to an output layer 590, which corresponds to an emotion represented by the image provided to the DLN 500. In one embodiment, the output layer 590 is a softmax output layer. A softmax function, or normalized exponential, is a generalization of the logistic function that "squashes" a K-dimensional vector of arbitrary real values to a K-dimensional vector of real values in the range. Since the components of the vector sum to one and are all strictly between zero and one, they represent a categorical probability distribution.

Figure 5B:
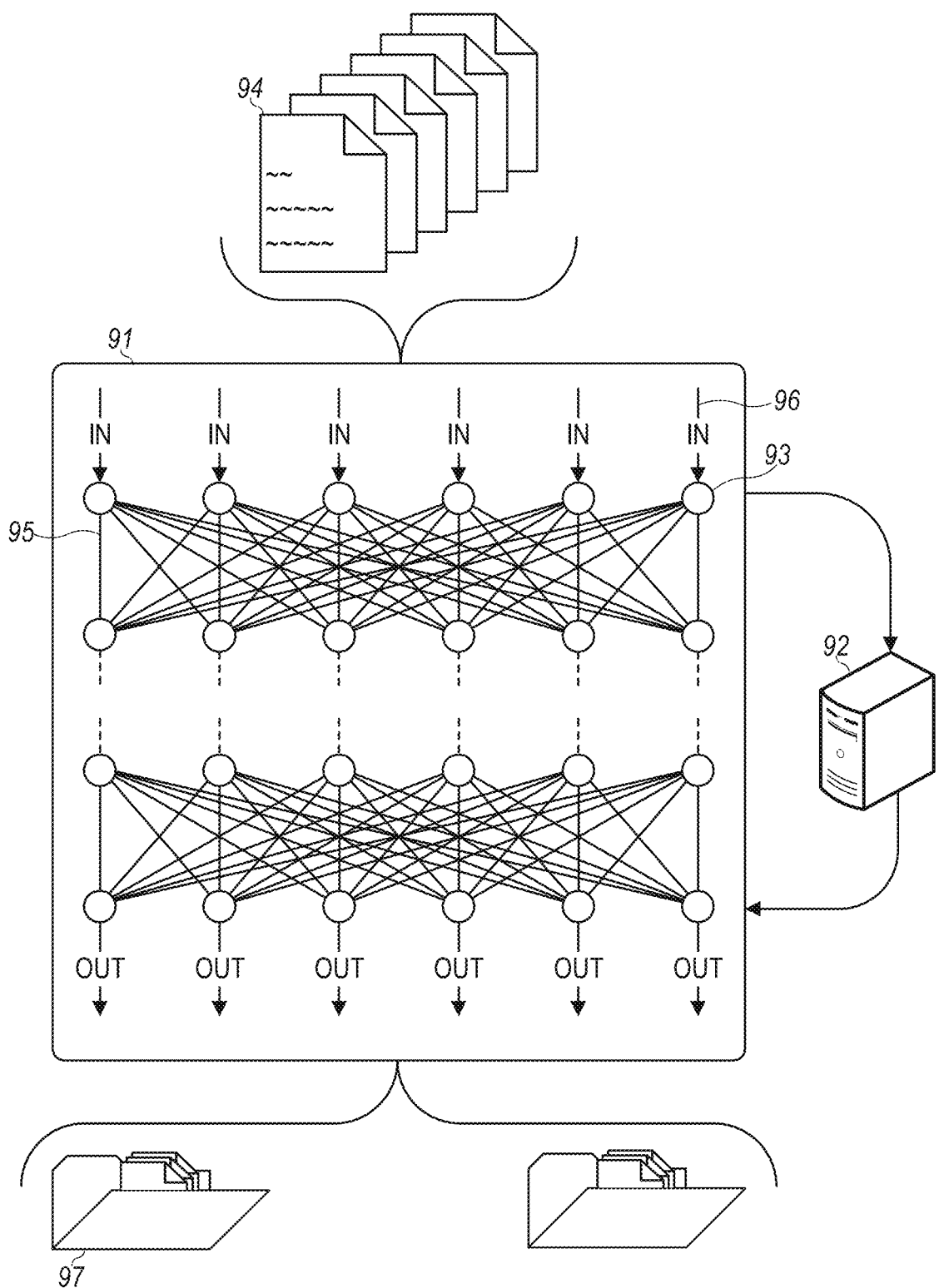
FIG. 5B is a block diagram of an example of an environment including a system for neural network training, according to an example embodiment.

FIG. 5B provides some background information regarding neural networks to aid in understanding operation of various embodiments, in particular the understanding of operation of image processing 352 in view of the details of input and output provided by FIG. 5A.

Image processing 352 may be implemented as a CNN, which takes labeled image data and identifies features in such images corresponding to feature labeled training data. Artificial intelligence (AI) is a field concerned with developing decision making systems to perform cognitive tasks that have traditionally required a living actor, such as a person. Artificial neural networks (ANNs) are computational structures that are loosely modeled on biological neurons. Generally, ANNs encode information (e.g., data or decision making) via weighted connections (e.g., synapses) between nodes (e.g., neurons). Modern ANNs are foundational to many AI applications, such as automated perception (e.g., computer vision, speech recognition, contextual awareness, etc.), automated cognition (e.g., decision-making, logistics, routing, supply chain optimization, etc.), automated control (e.g., autonomous cars, drones, robots, etc.), among others.

Many ANNs are represented as matrices of weights that correspond to the modeled connections. ANNs operate by accepting data into a set of input neurons that often have many outgoing connections to other neurons. At each traversal between neurons, the corresponding weight modifies the input and is tested against a threshold at the destination neuron. If the weighted value exceeds the threshold, the value is again weighted, or transformed through a nonlinear function, and transmitted to another neuron further down the ANN graph—if the threshold is not exceeded then, generally, the value is not transmitted to a down-graph neuron and the synaptic connection remains inactive. The process of weighting and testing continues until an output neuron is reached; the pattern and values of the output neurons constituting the result of the ANN processing.

The correct operation of most ANNs relies on correct weights. However, ANN designers do not generally know which weights will work for a given application. Instead, a training process is used to arrive at appropriate weights. ANN designers typically choose a number of neuron layers or specific connections between layers including circular connection as shown in FIG. 5A, but the ANN designer does not generally know which weights will work for a given application. Instead, a training process generally proceeds by selecting initial weights, which may be randomly selected. Training data (labeled images in this case) is fed into the ANN and results are compared to an objective function that provides an indication of error. The error indication is a measure of how wrong the ANN's result was compared to an expected result. This error is then used to correct the weights. Over many iterations, the weights will collectively converge to encode the operational data into the ANN. This process may be called an optimization of the objective function (e.g., a cost or loss function), whereby the cost or loss is minimized.

A gradient descent technique is often used to perform the objective function optimization. A gradient (e.g., partial derivative) is computed with respect to layer parameters (e.g., aspects of the weight) to provide a direction, and possibly a degree, of correction, but does not result in a single correction to set the weight to a "correct" value. That is, via several iterations, the weight will move towards the "correct," or operationally useful, value. In some implementations, the amount, or step size, of movement is fixed (e.g., the same from iteration to iteration). Small step sizes tend to take a long time to converge, whereas large step sizes may oscillate around the correct value, or exhibit other undesirable behavior. Variable step sizes may be attempted to provide faster convergence without the downsides of large step sizes.

Backpropagation is a technique whereby training data is fed forward through the ANN—here "forward" means that the data starts at the input neurons and follows the directed graph of neuron connections until the output neurons are reached—and the objective function is applied backwards through the ANN to correct the synapse weights. At each step in the backpropagation process, the result of the previous step is used to correct a weight. Thus, the result of the output neuron correction is applied to a neuron that connects to the output neuron, and so forth until the input neurons are reached. Backpropagation has become a popular technique to train a variety of ANNs. Any well known optimization algorithm for back propagation may be used, such as SGD, Adam, etc.

FIG. 5B is a block diagram of an example of an environment including a system for neural network training, according to an embodiment. The system includes an ANN 91 that is trained using a processing node 92. ANN 91 may be implemented as a module and used in conjunction with the combined reward functions. Example modules include convolutional neural networks (CNN) and other types of networks such as ResNet, a type of network that uses residual functions, as well as any other type of network that may be adapted to utilize reward functions. Such neural networks may consist of one or more layers of neurons or synapses in various embodiments. The number of layers may depend on the type of network selected. ResNet may have 50 layers, for example, while other networks may have from a few to a thousand or more. Other CNN structures that may be used include but are not limited to VGG, Inception, and Exception.

The processing node 92 may be a CPU, GPU, field programmable gate array (FPGA), digital signal processor (DSP), application specific integrated circuit (ASIC), or other processing circuitry. In an example, multiple processing nodes 92 may be employed to train different layers of the ANN 91, or even different nodes 93 within layers. Thus, a set of processing nodes 92 is arranged to perform the training of the ANN 91.

The set of processing nodes 92 is arranged to receive a training set 94 for the ANN 91. The ANN 91 comprises a set of nodes 93 arranged in layers (illustrated as rows of nodes 93) and a set of inter-node weights 95 (e.g., parameters) between nodes in the set of nodes. In an example, the training set 94 is a subset of a complete training set. Here, the subset may enable processing nodes with limited storage resources to participate in training the ANN 91.

The training data may include multiple numerical values representative of a domain, such as red, green, and blue pixel values and intensity values for an image or pitch and volume values at discrete times for speech recognition. Each value of the training, or input 96 to be classified once ANN 91 is trained, is provided to a corresponding node 93 in the first layer or input layer of ANN 91. The values propagate through the layers and are changed by the objective function.

As noted above, the set of processing nodes 92 is arranged to train the neural network to create a trained neural network. Once trained, data input into the ANN will produce valid classifications 97 (e.g., the input data 96 will be assigned into categories), for example. The training performed by the set of processing nodes 93 is iterative. In an example, each iteration of the training the neural network is performed independently between layers of the ANN 91.

Thus, two distinct layers may be processed in parallel by different members of the set of processing nodes. In an example, different layers of the ANN 91 are trained on different hardware.

ANN 91 may calculate one or more neuron or synapse weights 95 for criteria based upon one or more machine learning algorithms. During training, historical action information representing past actions of the robot may be labeled with an indication of whether the decision made was ultimately successful, in this case, the reward. Thus, the reward, which is based on both robot navigation and the ability to track the object, is used to update the network weights 95. Note that in various networks, initial weights may be pre-set. In other networks, initial weights may be randomized. In one embodiment, a module or processor executing computer instructions to effectuate the neural network learning operations modifies a source neuron's output with a synapse weight to determine the contribution of the source neuron to cause the sink neuron to fire. Practically, in this embodiment, a single and modified value is integrated at the sink neuron in response to the source neuron activation.

Figure 6A:
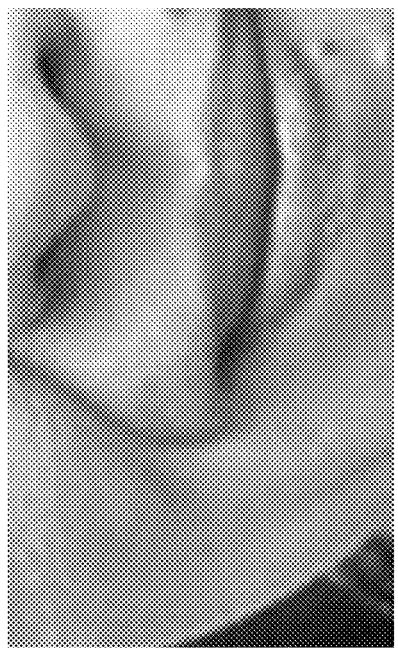
FIGS. 6A, 6B, 6C, 6D, 6E, 6F, 6G, and 6H are images of different skin conditions which can be representative of overall health of the person according to an example embodiment.
Figure 6B:
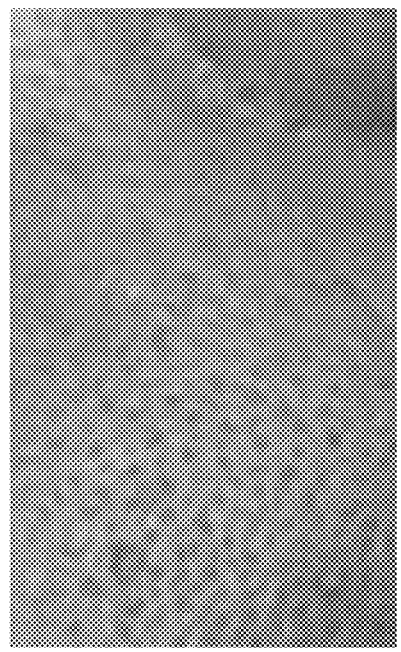
Figure 6C:
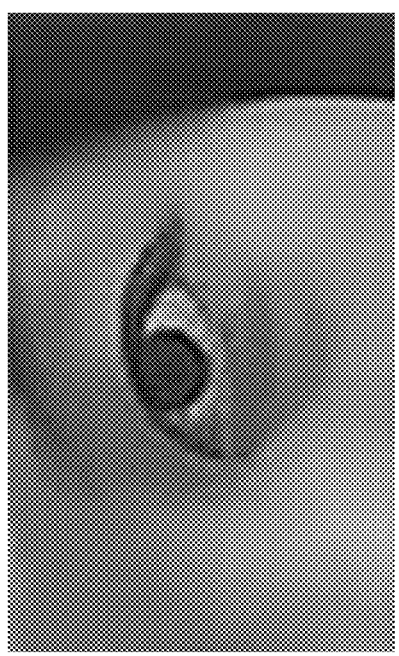
Figure 6D:
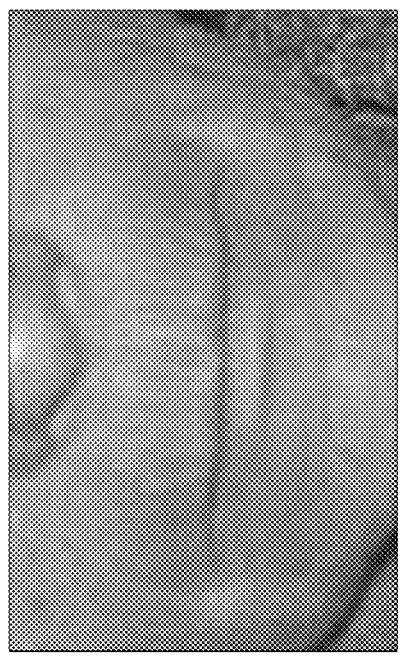
Figure 6F:
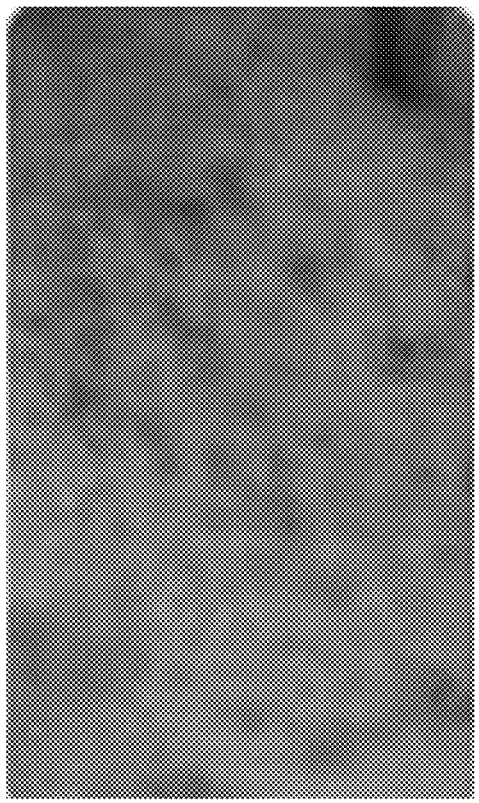
Figure 6H:
Figure 6E:
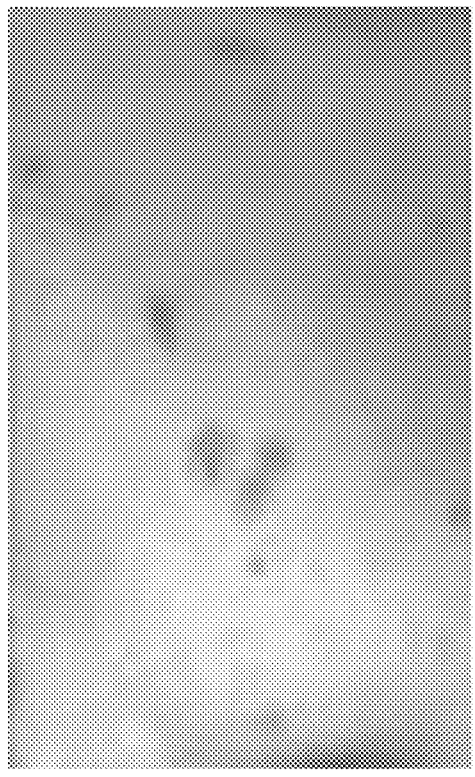
Figure 6G:

FIGS. 6A-H are images of different skin conditions which can be representative of overall health of the person. The DLN 500 may also be trained to detect such skin conditions using multiple images of each type of condition. FIG. 6A corresponds to wrinkles. FIG. 6B corresponds to skin sag. FIG. 6C corresponds to dark eyes. FIG. 6D corresponds to large skin pores. FIG. 6E corresponds to blemishes. FIG. 6F corresponds to acne. FIG. 6G corresponds to rosacea. FIG. 6H corresponds to scars. Further images may be used for recognizing skin cancer and other skin conditions. Such skin conditions may be used as other information 356, and fused with both the emotional and measured data information by fusion module 358 in system 300 as shown in FIG. 3.

Figure 7:
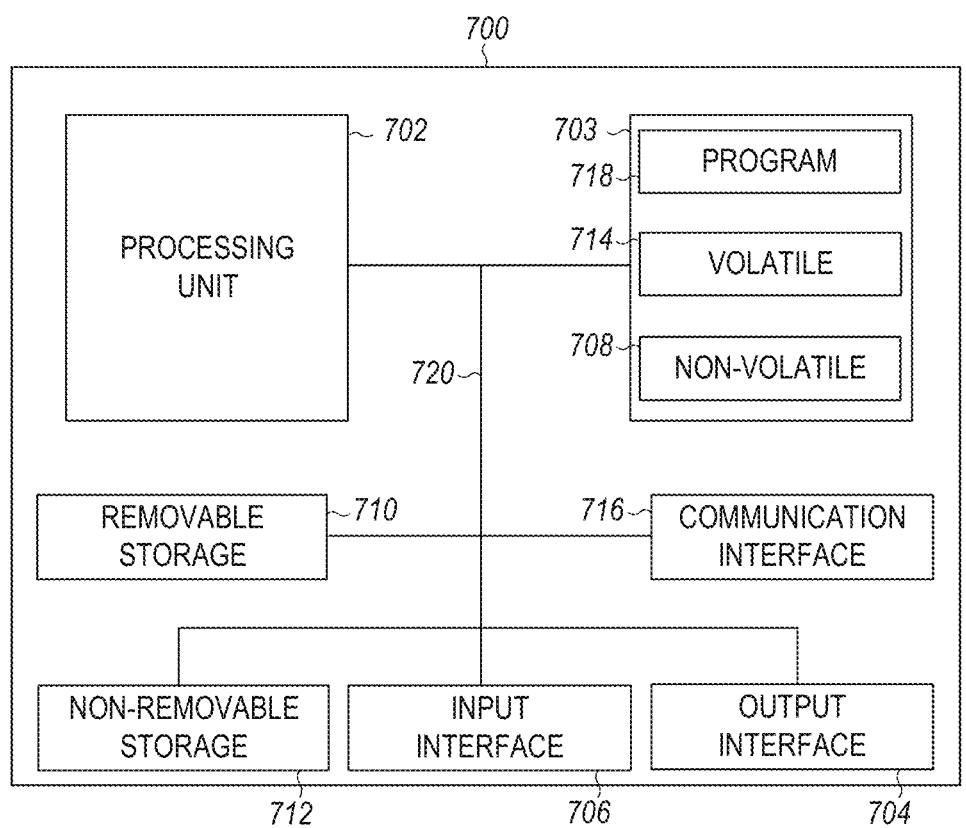
FIG. 7 is a block diagram illustrating circuitry for clients, servers, cloud based resources for implementing algorithms and performing methods according to example embodiments.

FIG. 7 is a block diagram illustrating circuitry for clients, servers, cloud based resources for implementing algorithms and performing methods according to example embodiments. All components need not be used in various embodiments. For example, the clients, servers, and network resources may each use a different set of components, or in the case of servers for example, larger storage devices.

One example computing device in the form of a computer 700 may include a processing unit 702, memory 703, removable storage 710, and non-removable storage 712. Although the example computing device is illustrated and described as computer 700, the computing device may be in different forms in different embodiments. For example, the computing device may instead be a smartphone, a tablet, smartwatch, or other computing device including the same or similar elements as illustrated and described with regard to FIG. 7. Devices, such as smartphones, tablets, and smartwatches, are generally collectively referred to as mobile devices or user equipment. Further, although the various data storage elements are illustrated as part of the computer 700, the storage may also or alternatively include cloud-based storage accessible via a network, such as the Internet or server based storage.

Memory 703 may include volatile memory 714 and non-volatile memory 708. Computer 700 may include—or have access to a computing environment that includes—a variety of computer-readable media, such as volatile memory 714 and non-volatile memory 708, removable storage 710 and non-removable storage 712. Computer storage includes random access memory (RAM), read only memory (ROM), erasable programmable read-only memory (EPROM) and electrically erasable programmable read-only memory (EEPROM), flash memory or other memory technologies, compact disc read-only memory (CD ROM), Digital Versatile Disks (DVD) or other optical disk storage, magnetic cassettes, magnetic tape, magnetic disk storage or other magnetic storage devices, or any other medium capable of storing computer-readable instructions.

Computer 700 may include or have access to a computing environment that includes input 706, output 704, and a communication connection 716. Output 704 may include a display device, such as a touchscreen, that also may serve as an input device. The input 706 may include one or more of a touchscreen, touchpad, mouse, keyboard, camera, one or more device-specific buttons, one or more sensors integrated within or coupled via wired or wireless data connections to the computer 700, and other input devices. The computer may operate in a networked environment using a communication connection to connect to one or more remote computers, such as database servers. The remote computer may include a personal computer (PC), server, router, network PC, a peer device or other common network node, or the like. The communication connection may include a Local Area Network (LAN), a Wide Area Network (WAN), cellular, WiFi, Bluetooth, or other networks.

Computer-readable instructions stored on a computer-readable medium are executable by the processing unit 702 of the computer 700. A hard drive, CD-ROM, and RAM are some examples of articles including a non-transitory computer-readable medium such as a storage device. The terms computer-readable medium and storage device do not include carrier waves to the extent carrier waves are deemed too transitory. Storage can also include networked storage such as a storage area network (SAN) indicated at 720.

EXAMPLES

According to one aspect of the present disclosure, and example includes a computer implemented method of generating a personalized health rating for a person uses one or more processors. The one or more processors execute instructions to perform the method including obtaining, by the one or more processors, measured data associated with the person, obtaining, by the one or more processors, a facial image of the person, extracting, by the one or more processors, emotional based features from the facial image, using a deep learning model trained on emotion labeled facial images to associate an emotional state with the extracted features to generate emotional data, and fusing, by the one or more processors, the measured data with the emotional data to generate the personalized health rating.

Optionally, in any of the preceding aspects, a further example includes normalizing the facial image prior to extracting the emotional based features such that the image is compatible with the measured data.

Optionally, in any of the preceding aspects, a further example includes removing noise from the image, wherein such noise comprises background pixels.

Optionally, in any of the preceding aspects, a further example includes wherein the deep learning model comprises a 3-layer convolutional neural network.

Optionally, in any of the preceding aspects, a further example includes wherein the facial image comprises multiple images captured by a networked camera.

Optionally, in any of the preceding aspects, a further example includes wherein the multiple images are captured continuously while the networked camera is enabled, and the personal health rating is calculated as a function of the multiple images.

Optionally, in any of the preceding aspects, a further example includes wherein the networked camera is incorporated in a wireless mobile device, and wherein the facial images are received from the mobile device.

Optionally, in any of the preceding aspects, a further example includes wherein the measured data comprises environmental data associated with the person, vital signs of the person, and daily activity of the person.

Optionally, in any of the preceding aspects, a further example includes wherein fusing the measured data and emotional data comprises using statistically sound information fusion with prioritized weighting of the data, and wherein the personalized health rating comprises a mental health rating.

According to one aspect of the present disclosure, a further example includes a device that includes a memory storage comprising instructions and one or more processors in communication with the memory. The one or more processors execute the instructions to obtain measured data associated with a person, obtain a facial image of the person, extract emotional based features from the facial image, use a deep learning model trained on emotion labeled facial images to associate an emotional state with the extracted features to generate emotional data, and fuse the measured data with the emotional data to generate a personalized health rating.

Optionally, in any of the preceding aspects, a further example includes normalizing the facial image prior to extracting the emotional based features such that the image is compatible with the measured data.

Optionally, in any of the preceding aspects, a further example includes wherein the deep learning model comprises a 3-layer convolutional neural network.

Optionally, in any of the preceding aspects, a further example includes a camera communicatively coupled to the processor to obtain the facial image, and wherein the facial image comprises multiple images.

Optionally, in any of the preceding aspects, a further example includes wherein fusing the measured data and emotional data comprises using statistically sound information fusion with prioritized weighting of the data and wherein the personalized health rating comprises a mental health rating.

Optionally, in any of the preceding aspects, a further example includes wherein the device is a wireless mobile device with an integrated camera.

According to one aspect of the present disclosure, a further example includes a non-transitory computer-readable media stores computer instructions for generating a personalized health rating. When the instructions are executed by one or more processors, the one or more processors perform the steps of obtaining measured data associated with a person, obtaining a facial image of the person, extracting emotional based features from the facial image, using a deep learning model trained on emotion labeled facial images to associate an emotional state with the extracted features to generate emotional data, and fusing the measured data with the emotional data to generate the personalized health rating.

Optionally, in any of the preceding aspects, a further example includes normalizing the facial image prior to extracting the emotional based features such that the image is compatible with the measured data.

Optionally, in any of the preceding aspects, a further example includes removing noise from the image, wherein such noise comprises background pixels.

Optionally, in any of the preceding aspects, a further example includes wherein the deep learning model comprises a 3-layer convolutional neural network.

Optionally, in any of the preceding aspects, a further example includes wherein the facial image comprises multiple images captured by a networked camera and wherein fusing the measured data and emotional data comprises using statistically sound information fusion with prioritized weighting of the data and wherein the personalized health rating comprises a mental health rating.

EXAMPLES

In example 1, a computer implemented method of generating a personalized health rating for a person using one or more processors, the method including obtaining, by the one or more processors, measured data associated with the person, obtaining, by the one or more processors, a facial image of the person, extracting, by the one or more processors, emotional based features from the facial image, using a deep learning model trained on emotion labeled facial images to associate an emotional state with the extracted features to generate emotional data, and fusing, by the one or more processors, the measured data with the emotional data to generate the personalized health rating.

Example 2 includes the method of example 1 and further comprising normalizing the facial image prior to extracting the emotional based features such that the image is compatible with the measured data.

Example 3 includes the method of any of examples 1-2 and further comprising removing noise from the image, wherein such noise comprises background pixels.

Example 4 includes the method of any of examples 1-3 wherein the deep learning model comprises a 3-layer convolutional neural network.

Example 5 includes the method of any of examples 1-4 wherein the facial image comprises multiple images captured by a networked camera.

Example 6 includes the method of example 5 wherein the multiple images are captured continuously while the networked camera is enabled, and the personal health rating is calculated as a function of the multiple images.

Example 7 includes the method of any of examples 5-6 wherein the networked camera is incorporated in a wireless mobile device, and wherein the facial images are received from the mobile device.

Example 8 includes the method of any of examples 1-7 wherein the measured data comprises environmental data associated with the person, vital signs of the person, and daily activity of the person.

Example 9 includes the method of any of examples 1-8 wherein fusing the measured data and emotional data comprises using statistically sound information fusion with prioritized weighting of the data, and wherein the personalized health rating comprises a mental health rating.

In example 10, a device includes a memory storage comprising instructions, and one or more processors in communication with the memory, wherein the one or more processors execute the instructions to obtain measured data associated with a person, obtain a facial image of the person, extract emotional based features from the facial image, use a deep learning model trained on emotion labeled facial images to associate an emotional state with the extracted features to generate emotional data, and fuse the measured data with the emotional data to generate a personalized health rating.

Example 11 includes the device of example 10 and further comprising normalizing the facial image prior to extracting the emotional based features such that the image is compatible with the measured data.

Example 12 includes the device of any of examples 10-11 wherein the deep learning model comprises a 3-layer convolutional neural network.

Example 13 includes the device of any of examples 10-12 and further comprising a camera communicatively coupled to the processor to obtain the facial image, and wherein the facial image comprises multiple images.

Example 14 includes the device of any of examples 10-13 wherein fusing the measured data and emotional data comprises using statistically sound information fusion with prioritized weighting of the data and wherein the personalized health rating comprises a mental health rating.

Example 15 includes the device of any of examples 10-14 wherein the device is a wireless mobile device with an integrated camera.

In example 16, a non-transitory computer-readable media storing computer instructions for generating a personalized health rating, that when executed by one or more processors, cause the one or more processors to perform the steps of obtaining measured data associated with a person, obtaining a facial image of the person, extracting emotional based features from the facial image, using a deep learning model trained on emotion labeled facial images to associate an emotional state with the extracted features to generate emotional data, and fusing the measured data with the emotional data to generate the personalized health rating.

Example 17 includes the non-transitory computer-readable media of example 16 and further comprising normalizing the facial image prior to extracting the emotional based features such that the image is compatible with the measured data.

Example 18 includes the non-transitory computer-readable media of any of examples 16-17 and further comprising removing noise from the image, wherein such noise comprises background pixels.

Example 19 includes the non-transitory computer-readable media of any of examples 16-17 wherein the deep learning model comprises a 3-layer convolutional neural network.

Example 20 includes the non-transitory computer-readable media of any of examples 16-19 wherein the facial image comprises multiple images captured by a networked camera and wherein fusing the measured data and emotional data comprises using statistically sound information fusion with prioritized weighting of the data and wherein the personalized health rating comprises a mental health rating.

Although a few embodiments have been described in detail above, other modifications are possible. For example, the logic flows depicted in the figures do not require the particular order shown, or sequential order, to achieve desirable results. Other steps may be provided, or steps may be eliminated, from the described flows, and other components may be added to, or removed from, the described systems. Other embodiments may be within the scope of the following claims.

What is claimed is:

1. A computer implemented method of generating a personalized health rating for a person using one or more processors, the method comprising:
   obtaining, by the one or more processors, measured data associated with the person;
   obtaining, by the one or more processors, multiple time stamped facial images of the person;
   extracting, by the one or more processors, emotional based features from the facial image;
   using a deep learning model trained on emotion labeled facial images to associate an emotional state with the extracted features of each of the multiple images to determine an amount of time the person is in the emotional state to generate emotional data; and
   fusing, by the one or more processors, the measured data with the emotional data to generate the personalized health rating that includes a mental health rating.

2. The method of claim 1 and further comprising normalizing the facial image prior to extracting the emotional based features such that the image is compatible with the measured data.

3. The method of claim 1 and further comprising removing noise from the image, wherein such noise comprises background pixels.

4. The method of claim 1 wherein the deep learning model comprises a 3-layer convolutional neural network.

5. The method of claim 1 wherein the multiple images are captured continuously while the networked camera is enabled, and the personal health rating is calculated as a function of the multiple images.

6. The method of claim 1 wherein the networked camera is incorporated in a wireless mobile device, and wherein the facial images are received from the mobile device.

7. The method of claim 1 wherein the measured data comprises environmental data associated with the person, vital signs of the person, and daily activity of the person.

8. The method of claim 1 wherein fusing the measured data and emotional data comprises using statistically sound information fusion with prioritized weighting of the data.

9. A device, comprising:
   a memory storage comprising instructions; and
   one or more processors in communication with the memory, wherein the one or more processors execute the instructions to:
   obtain measured data associated with a person;
   obtain multiple time stamped facial images of the person;
   extract emotional based features from the facial image;
   use a deep learning model trained on emotion labeled facial images to associate an emotional state with the extracted features of each of the multiple images to determine an amount of time the person is in the emotional state to generate emotional data; and
   fuse the measured data with the emotional data to generate a personalized health rating that includes a mental health rating.

10. The device of claim 9 and further comprising normalizing the facial image prior to extracting the emotional based features such that the image is compatible with the measured data.

11. The device of claim 9 wherein the deep learning model comprises a 3-layer convolutional neural network.

12. The device of claim 9 and further comprising a camera communicatively coupled to the processor to obtain the facial image.

13. The device of claim 9 wherein fusing the measured data and emotional data comprises using statistically sound information fusion with prioritized weighting of the data.

14. The device of claim 9 wherein the device is a wireless mobile device with an integrated camera.

15. A non-transitory computer-readable media storing computer instructions for generating a personalized health rating, that when executed by one or more processors, cause the one or more processors to perform the steps of:
   obtaining measured data associated with a person;

obtaining multiple time stamped facial images of the person;

extracting emotional based features from the facial image;

using a deep learning model trained on emotion labeled facial images to associate an emotional state with the extracted features of each of the multiple images to determine an amount of time the person is in the emotional state to generate emotional data; and fusing the measured data with the emotional data to generate the personalized health rating that includes a mental health rating.

16. The non-transitory computer-readable media of claim 15 and further comprising normalizing the facial image prior to extracting the emotional based features such that the image is compatible with the measured data.

17. The non-transitory computer-readable media of claim 15 and further comprising removing noise from the image, wherein such noise comprises background pixels.

18. The non-transitory computer-readable media of claim 15 wherein the deep learning model comprises a 3-layer convolutional neural network.

19. The non-transitory computer-readable media of claim 15 wherein fusing the measured data and emotional data comprises using statistically sound information fusion with prioritized weighting of the data.

* * * * *